(12) United States Patent
Zoll et al.

(10) Patent No.: US 10,667,802 B2
(45) Date of Patent: Jun. 2, 2020

(54) DEVICES AND METHODS FOR JOINING TISSUE

(71) Applicant: Boston Scientific Scimed, Inc., Maple Grove, MN (US)

(72) Inventors: Jonathan Zoll, Brookline, MA (US); Michael S. H. Chu, Brookline, MA (US); Peter J. Pereira, Mendon, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 234 days.

(21) Appl. No.: 15/171,830

(22) Filed: Jun. 2, 2016

(65) Prior Publication Data
US 2016/0354075 A1   Dec. 8, 2016

Related U.S. Application Data

(60) Provisional application No. 62/171,664, filed on Jun. 5, 2015.

(51) Int. Cl.
  *A61B 17/04*   (2006.01)
  *A61B 17/34*   (2006.01)
  *A61B 17/00*   (2006.01)

(52) U.S. Cl.
  CPC ...... *A61B 17/0401* (2013.01); *A61B 17/3468* (2013.01); *A61B 2017/00805* (2013.01);
  (Continued)

(58) Field of Classification Search
  CPC ........ A61B 17/0401; A61B 2017/0409; A61B 2017/0438; A61B 2017/0445; A61B 2017/00867
  See application file for complete search history.

(56) References Cited

U.S. PATENT DOCUMENTS

| 5,290,297 A * | 3/1994 | Phillips ................ A61B 17/064 24/711.1 |
| 2011/0306989 A1 | 12/2011 | Darois et al. |
| 2012/0022557 A1 | 1/2012 | Cabiri et al. |

FOREIGN PATENT DOCUMENTS

WO   2014033692 A2   3/2014

OTHER PUBLICATIONS

International Preliminary Report on Patentability for International Application No. PCT/US2016/035703, dated Dec. 14, 2017, 12 pages.

(Continued)

*Primary Examiner* — Thomas McEvoy
(74) *Attorney, Agent, or Firm* — Brake Hughes Bellermann LLP (57) ABSTRACT

A medical device may include a luminal body defining a working channel extending between a proximal end of the luminal body and a distal end of the luminal body. The device may also include a carrier defining a pusher thereon. The carrier may be configured to transition between a first state and a second state. In the first state, a distal portion of the carrier may extend within the working channel along a central longitudinal axis thereof. In the second state, the distal portion of the carrier may extend distally of the luminal body. The device may also include a plurality of anchors which may be disposed about the carrier. Also, at least a distal-most anchor of the plurality of anchors may define a surface configured to cooperate with the pusher and further defines a curved wall configured to cooperate with the pusher to rotate the plurality of anchors.

15 Claims, 7 Drawing Sheets

(52) U.S. Cl.
CPC ............... *A61B 2017/00867* (2013.01); *A61B 2017/0409* (2013.01); *A61B 2017/0445* (2013.01); *A61B 2017/0464* (2013.01)

(56) References Cited

OTHER PUBLICATIONS

International Search Report and Written Opinion for PCT Application No. PCT/US2016/035703, dated Nov. 29, 2016, 17 pages.
Invitation to Pay Add'l Fees and Partial Search Report for PCT Application No. PCT/US2016/035703, dated Sep. 29, 2016, 8 pages.

\* cited by examiner

DEVICES AND METHODS FOR JOINING TISSUE

CROSS-REFERENCE TO RELATED APPLICATION(S)

This application is a Nonprovisional of, and claims priority to, U.S. Patent Application No. 62/171,664, filed on Jun. 5, 2015, entitled "DEVICES AND METHODS FOR JOINING TISSUE", which is incorporated by reference herein in its entirety.

TECHNICAL FIELD

The disclosure relates generally to devices and methods for joining tissue, and, more specifically, delivering one or more anchors to join tissue.

BACKGROUND

A variety of medical procedures are performed to provide support to portions of a body of a patient. For example, some medical procedures are performed to treat various pelvic dysfunctions, including procedures to treat urinary incontinence, and correcting various prolapse conditions such as uterine prolapse, cystoceles, rectoceles, and vaginal vault prolapse.

Treatments of such dysfunctions have included suturing procedures and/or the use of implants (e.g., mesh) for support or suspension of a portion of a body of a patient. Such suturing and/or implant placing can be difficult and time intensive. Accordingly, such procedures may be very costly. Additionally, due to the level of difficulty, many such procedures are performed by highly skilled physicians which may further increase the cost of the procedure.

The device and methods of the current disclosure may rectify some of the deficiencies described above or other deficiencies in the art.

SUMMARY

Aspects of the present disclosure relate to, among other things, medical devices and related methods for joining tissue. Each of the embodiments disclosed herein may include one or more of the features described in connection with any of the other disclosed embodiments.

In one aspect, a medical device may include a luminal body defining a working channel extending between a proximal end of the luminal body and a distal end of the luminal body. The device may also include a carrier defining a pusher thereon. The carrier may be configured to transition between a first state and a second state. In the first state, a distal portion of the carrier may extend within the working channel along a central longitudinal axis thereof. In the second state, the distal portion of the carrier may extend distally of the luminal body. The device may also include a plurality of anchors. Each anchor of the plurality of anchors may be disposed about the carrier. Also, at least a distal-most anchor of the plurality of anchors may define a surface configured to cooperate with the pusher and further defines a curved wall configured to cooperate with the pusher to rotate the plurality of anchors.

The medical device may include any one or more of the following features: the carrier may be comprised of a shape memory material; in the second state, the distal portion of the carrier may curve away from the central longitudinal axis of the working channel; the carrier may have a distal tip configured to pierce tissue; the distal tip of the carrier may be configured to be passed through a central lumen of each of the plurality of anchors; the plurality of anchors may comprise at least the distal most anchor and a travel anchor, wherein the travel anchor may be coupled to the distal most anchor via at least one suture member; each anchor of the plurality of anchors may define a surface configured to cooperate with the pusher, and each anchor of the plurality of anchors may define a curved wall configured to cooperate with the pusher to rotate the plurality of anchors; each anchor of the plurality of anchors may be coupled to an adjacent anchor of the plurality of anchors via at least one suture member; a handle may be coupled to the proximal end of the luminal body and include an actuator operably coupled with the carrier to move the carrier between the first and second states; the actuator may be operably coupled to the carrier via a cam follower mechanism; each anchor of the plurality of anchors may define a proximal extension and a distal recess; the proximal extension of each anchor of the plurality of anchors may be configured to be matingly received within the distal recess of an adjacent anchor of the plurality of anchors; the proximal extension and distal recess of at least some of the plurality of anchors may be radially offset from one another while the proximal extension and distal recess of the remaining anchors of the plurality of anchors may be aligned along a common axis; the proximal extension and distal recess of each of the plurality of anchors may be radially offset from one another; and each anchor of the plurality of anchors may be rotatably disposed about the carrier.

In another exemplary aspect, a method may include advancing a carrier distally of a working channel of a medical device comprising a luminal body defining the working channel so as to cause the carrier to transition between a first state and a second state. In the first state, a distal portion of the carrier may extend within the working channel along a central longitudinal axis thereof. In the second state, the distal portion of the carrier may extend distally of the working channel. The method may further include positioning at least one anchor of a plurality of anchors adjacent tissue to be joined. Each anchor of the plurality of anchors may be disposed about the carrier. Also, at least a distal-most anchor of the plurality of anchors may define a surface configured to cooperate with a pusher on an external surface of the carrier. Further, at least the distal-most anchor of the plurality of anchors may define a curved wall which may be configured to cooperate with the pusher to rotate the plurality of anchors.

The method may include any one or more of the following features: positioning the at least one anchor of the plurality of anchors may include engaging the pusher with the surface so as to distally advance the at least one anchor while advancing the carrier; advancing the carrier may include actuating a cam follower mechanism; the carrier may be comprised of a shape memory material; and each anchor of the plurality of anchors may be coupled to an adjacent anchor of the plurality of anchors via at least one suture member.

In another exemplary aspect, a medical device may include a luminal body defining a working channel extending between a proximal end of the luminal body and a distal end of the luminal body. The medical device may further include a revolver defining a plurality of revolver chambers therein. The revolver may be rotatably coupled to the distal end of the luminal body. Also, a carrier may be configured to transition between a first state and a second state. In the first state, a distal portion of the carrier may extend within the working channel along a central longitudinal axis thereof. In the second state, the distal portion of the carrier may extend distally of the luminal body and revolver. Further, the medical device may include a plurality of anchors. At least one anchor of the plurality of anchors may be positioned within each revolver chamber of the plurality of revolver chambers. A handle assembly may include an actuator operably coupled with the carrier and an energy transmission element operably coupled with the revolver. Also, linear movement of the carrier may result in rotational movement of the revolver via the energy transmission element.

The medical device may include any one or more of the following features: the carrier may be comprised of a shape memory material; and the revolver may define six revolver chambers.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Overview

Examples of the present disclosure relate to medical devices and methods of treating internal areas of a subject's body. The medical devices and methods may facilitate joining of tissue.

Detailed Examples

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body.

Figure 1:
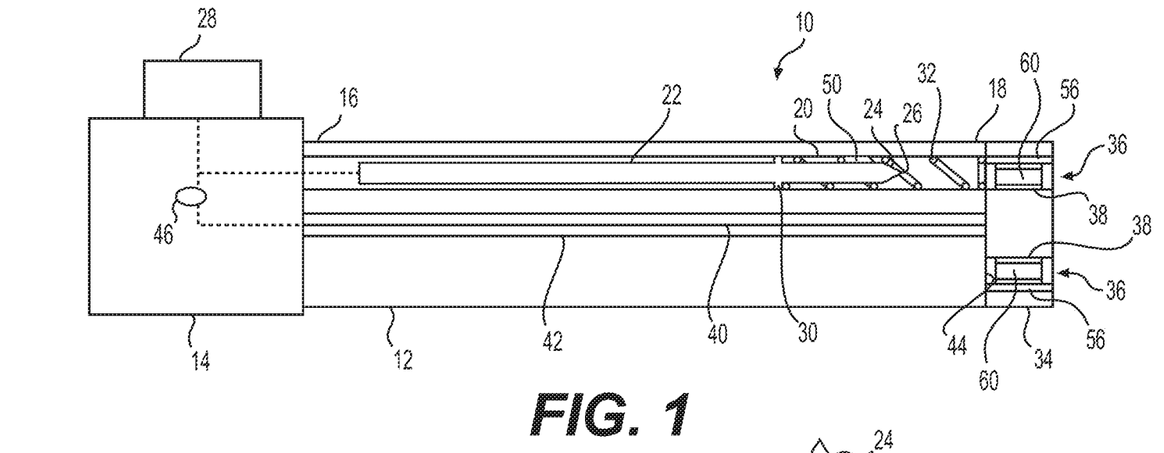
FIG. 1 illustrates a medical device according to a first exemplary aspect of the disclosure.

FIG. 1 is a schematic illustration of a medical device 10 according to an aspect of the present disclosure. Medical device 10 may include a luminal body 12 coupled to a handle 14. Luminal body 12 may be configured to traverse anatomical lumens of the subject's body. Luminal body 12 may include a circular, ovular, irregular, and/or any other cross-sectional shape appropriate for insertion within anatomical lumens of the subject's body, and/or combinations thereof.

Luminal body 12 may include a proximal end 16, a distal end 18, and define a plurality of channels extending between proximal end 16 and distal end 18. For example, luminal body 12 may include at least one working channel 20. While only a single working channel 20 is depicted, it is understood that any number of working channels 20 may be included. Working channel 20 may be configured to movably receive a carrier 22 therein.

Carrier 22 may comprise a longitudinally-extending member such as, for example, a rod. Carrier 22 may be comprised of shape memory material. Shape-memory material is a material that can be formed into a particular shape, retain that shape during resting conditions (e.g., when the shaped material is not subject to external forces or when external forces applied to the shaped material are insufficient to substantially deform the shape), be deformed into a second shape when subjected to a sufficiently strong external force, and revert substantially back to the initial shape when external forces are no longer applied. Examples of shape memory materials include synthetic plastics, stainless steel, and superelastic metallic alloys of nickel/titanium (e.g., Nitinol), copper, cobalt, vanadium, chromium, iron, or the like. Also, combinations of these and other materials can be used.

As shown in FIG. 1, carrier 22 may include a key 50 as will be described in further detail below. Also, carrier 22 may include a tip 24 which is sharp or pointed such that tip 24 may be configured to pierce bodily tissue as carrier 22 is advanced, as will be described in further detail. As shown in FIG. 1, tip 24 may taper distally towards a central distalmost point 26. However, it is understood that tip 24 may have alternative constructions.

Figure 2:
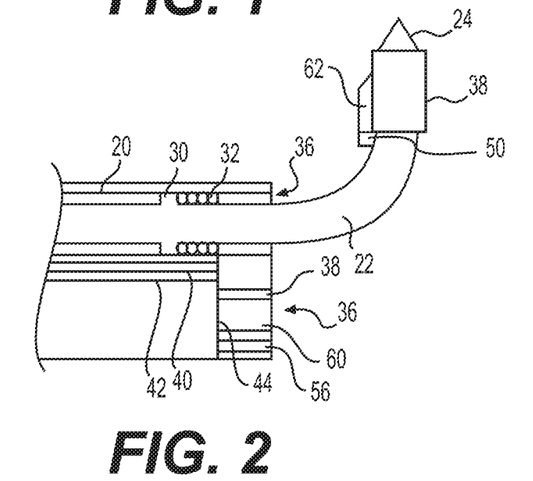
FIG. 2 illustrates a distal portion of the medical device of FIG. 1 after transitioning from a first state to a second state.

Carrier 22 may be operatively coupled to an actuator 28 configured to move the carrier 22 between an extended state (FIG. 2) and a retracted state (FIG. 1). For example, manipulation of actuator 28 in a first direction (e.g., distally), may move carrier 22 distally along and through working channel 20 and a selected revolver chamber 36, such that at least a portion of carrier 22 including tip 24 extends distally of a revolver 34, as described in further detail below. Once carrier 22 extends distally of revolver 34, carrier 22 is free to return to its memory configuration. For example, as shown in FIG. 2, carrier 22 may have a rounded, arcuate, bent, or otherwise curved memory configuration. As such, upon exiting working channel 20 and revolver 34, carrier 22 is no longer restrained toward a linear configuration, but may return to its memory curved configuration. In so doing, carrier 22, including tip 24, may pierce through tissue so as to place an anchor 38, as will be described in further detail below. Additionally, manipulation of actuator 28 in a second direction (e.g., proximally), may cause carrier 22 to move proximally and return towards its retracted state (e.g., a linear configuration) within working channel 20, as shown in FIG. 1. Alternatively, in some examples, manipulation of actuator 28 in a first direction (e.g., distally) may cause carrier 22 to move proximally, while manipulation of actuator 28 in a second direction (e.g., proximally) may cause carrier 22 to move distally. While actuator 28 is illustrated schematically in FIG. 1, it is understood that actuator 28 may include, by way of non-limiting example, at least one of a slider, a push button, a two-way rocker, a plunger, or any combination thereof.

In some examples, carrier 22 may be biased towards its retracted state as shown in FIG. 1. As such, carrier 22 may include a stop member 30 extending radially outwardly of a central longitudinal axis of carrier 22 in the retracted state. Stop member 30 may comprise a protrusion, extension, or any other such component configured to cooperate with a spring 32, at least a portion of which is positioned about carrier 22. For example, spring 32 may be positioned within working channel 20, towards distal end 18 of luminal body 12. When in the retracted state, stop member 30 may rest and/or abut against a proximal end of spring 32 such that spring 32 urges stop member 30, and therefore carrier 22, towards its retracted state within working channel 20. When a user determines a need to move carrier 22 towards its extended state (e.g., when a user determines a need to either pierce tissue and/or place an anchor 38), he/she must apply a force on actuator 28 sufficient to overcome the force of spring 32. Upon application of such a force, stop member 30 may be urged distally against spring 32, thereby compressing spring 32. As spring 32 compresses, a portion of carrier 22 may extend through spring 32, along working channel 20, and through revolver chamber 36 to move towards its extended state, as shown in FIG. 2. Upon releasing actuator 28, spring 32 may be free to expand and consequently, urge carrier 22 to return towards its retracted state. Accordingly, carrier 22 may automatically return from its extended state to its retracted state by virtue of spring 32.

Figure 3:
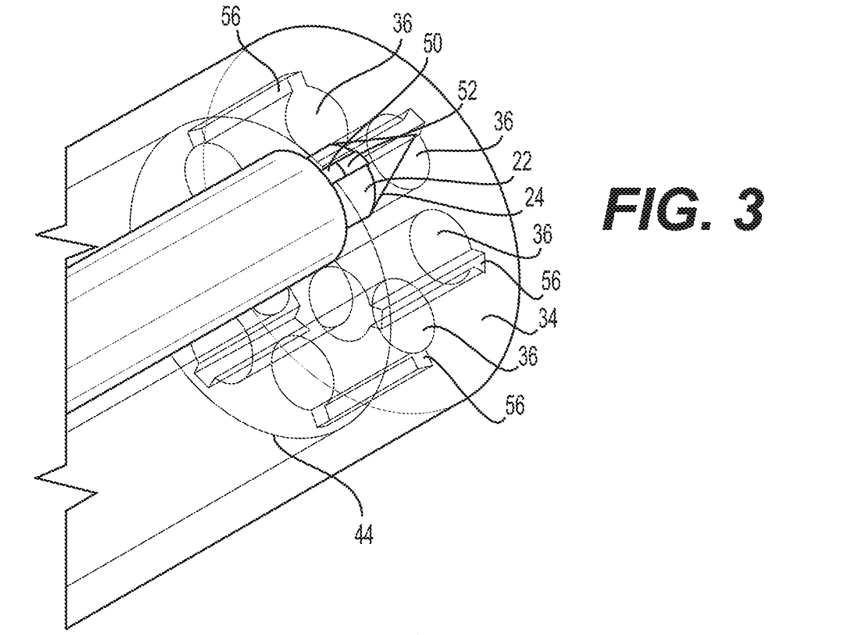
FIG. 3 illustrates a perspective view of a distal end of the medical device of FIG. 1.
Figure 4:
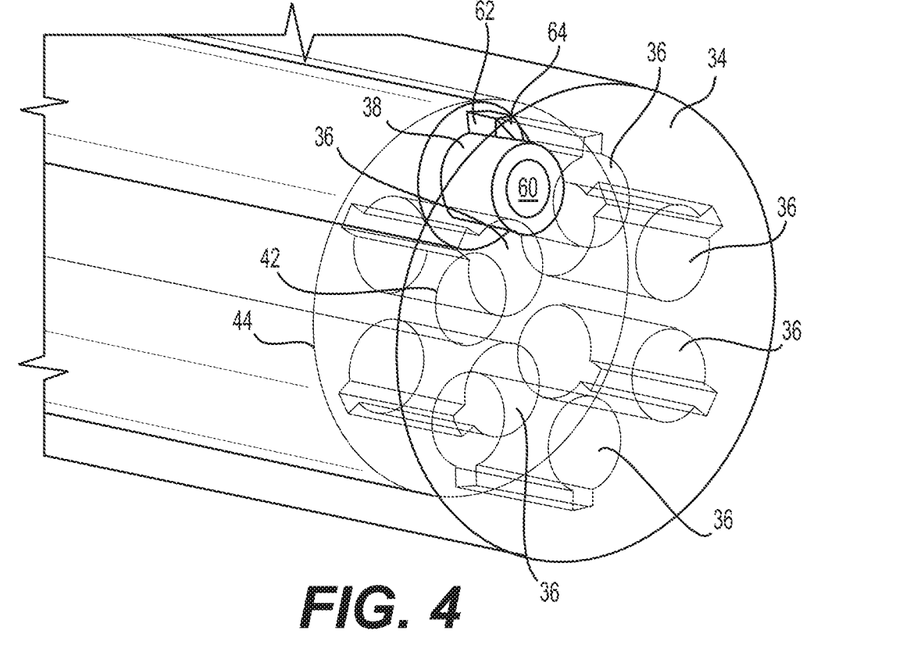
FIG. 4 illustrates an alternative perspective view of the distal end of the medical device of FIG. 1.

As shown in FIG. 1, a revolver 34 may be coupled to distal end 18 of luminal body 12. Revolver 34 may define a plurality of revolver chambers 36 extending therethrough. Revolver 34 may include any appropriate number of revolver chambers 36 for housing a desired number of anchors 38, as will be discussed in further detail below. For example, revolver 34 may include six revolver chambers 36, as shown in FIGS. 3 and 4. More or fewer revolver chambers 36 may be used without departing from the scope of this disclosure. Each anchor 38 may define a lumen 60 and include a key 62, as will be described in further detail below. Additionally, each revolver chamber 36 may include a key slot 56 as will be described in further detail below.

Revolver 34 may be rotatably coupled to luminal body 12. Accordingly, each revolver chamber 36 may be sequentially aligned with working channel 20 such that carrier 22 may be actuated to deploy each anchor 38 (FIG. 4) positioned within each revolver chamber 36, as explained in further detail below. Revolver 34 may be rotated via a revolver rod 40 extending through a revolver rod lumen 42 within luminal body 12. As shown in FIG. 1, revolver rod lumen 42 may extend along a central longitudinal axis of luminal body 12, parallel to working channel 20, from proximal end 16 to distal end 18 of luminal body 12. Revolver rod 40 may be fixedly coupled with a proximal end 44 of revolver 34. For example, as shown in FIG. 1, revolver rod 40 may extend from proximal end 44, through revolver lumen 42, and towards handle 14.

In order to turn revolver rod 40, and consequently, revolver 34, revolver rod 40 may be selectively coupled to carrier 22 via an energy transmission element 46 positioned within handle 14. Energy transmission element 46 may be any appropriate element configured to convert a linear force into a rotational force. Examples of such energy transmission elements 46 may include, but are not limited to, a rack and pinion system, a crank, a screw drive, a gearing system, a linkage system, a cam follower mechanism, and any appropriate combinations thereof.

Energy transmission element 46 may be configured to convert the linear motion created when carrier 22 returns from the extended state (FIG. 2) towards the retracted state (FIG. 1). That is, following actuation of carrier 22 via actuator 28 from the carrier 22 retracted state towards the carrier 22 extended state, a user may release actuator 28. Once actuator 28 is released, and/or application of force on actuator 28 has been ceased by the user, carrier 22 is caused to return towards the retracted state via spring 32, as described above. The linear motion of carrier 22 as it moves proximally may be converted to rotational motion via energy transmission element 46, which in turn causes revolver rod 40 to rotate a pre-determined amount, thus moving a first revolver chamber 36 from a position aligned with working channel 20 to a position out of alignment with working channel 20, while moving a second revolver chamber 36 into alignment with working channel 20. By way of example only, the angular amount of rotation revolver rod 40 travels each time carrier 22 returns towards its retracted state may depend on the number of revolver chambers 36 defined by the revolver 34. For example, in arrangements in which revolver 34 includes six revolver chambers 36, revolver rod 40 may rotate 60° (e.g., ⅙th of a complete 360° rotation). If the revolver 34 defines more or less revolver chambers 36, energy transmission element 46 may be configured to rotate revolver rod 40 through a smaller or larger degree of rotation, respectively. Accordingly, revolver 34 is automatically rotated following each activation of carrier 22 via actuator 28 and energy transmission element 46.

In some examples, however, energy transmission element 46 may be omitted. In such cases, a user may manually rotate revolver rod 40, and consequently, revolver 36, via an additional actuator (not shown) on handle 14. For example, following each actuation of carrier 22 via actuator 28, a user may selectively determine to rotate revolver 34. That is, rather than the activation of carrier 22 and the rotation of revolver 34 being performed by a single user action, the user may be required to perform two separate actions, activation of carrier 22 via actuator 28 and rotation of revolver 34 via an additional actuator (not shown) on handle 14.

As shown in FIGS. 3 and 4, each revolver chamber 36 may be dimensioned and/or shaped so as to cooperate with carrier 22 and an anchor 38. For example, As shown in FIG. 3, carrier 22 may include a key 50 extending radially outwardly from a central axis of carrier 22. It is understood that while key 50 is illustrated as an elongate bar-shaped member in FIG. 3, other key 50 shapes and structures are within the scope of this disclosure. Additionally, at least a portion 52 of key 50 may be angled, sloped, tapered, arcuate and/or otherwise shaped so as to facilitate smooth engagement with an anchor 38, as will be described in further detail below. In addition, each revolver chamber 36 may have a key slot and/or hole 56 configured to cooperate with key 50 of carrier 22 so as to guide carrier 22 as carrier 22 moves towards its extended state. As shown in FIGS. 3 and 4, each key slot 56 of each revolver chamber 36 is configured to correspond in shape to key 50 of carrier 22. In other words, each key slot 56 may be configured to receive key 50 of carrier 22 therein when carrier 22 is moved between the retracted and extended states. Accordingly, each key slot 56 may cooperate with key 50 of carrier 22 so as to guide carrier 22 as it travels between the retracted and extended states.

An exemplary anchor 38 is depicted in FIG. 4. While only one such anchor 38 is depicted in a first revolver chamber 36, it is understood that each revolver chamber 36 may be configured to retain an anchor 38 therein. For example, in a revolver 34 comprising six revolver chambers 36, each revolver chamber 36 may include at least one anchor 38, therein. Accordingly, revolver 34 may house, contain, or otherwise include at least six anchors 38. In order to prevent anchors 38 from being inadvertently dislodged from revolver 34, e.g., prior to intentional deployment of anchor (s) 38 via actuator 28, a frangible and/or piercable cover or film (not shown) may be disposed on the distal end of revolver 34. The cover or film may be punctured as the carrier 22 is actuated via actuator 28. Alternatively, luminal body 12 may be coupled with a cap (not shown) positioned on the distal end of revolver 34 such that the cap is fixed with respect to luminal body 12 while revolver 34 rotates with respect to the cap. The cap may define a single opening aligned with working channel 20 such that only the anchor 38 positioned in the revolver chamber 36 aligned with working channel 20 may be deployed, while any remaining anchors 38 in any remaining revolver chamber 36 may be prevented from inadvertently being dislodged and/or falling out of revolver 34.

Figures 5, 6:
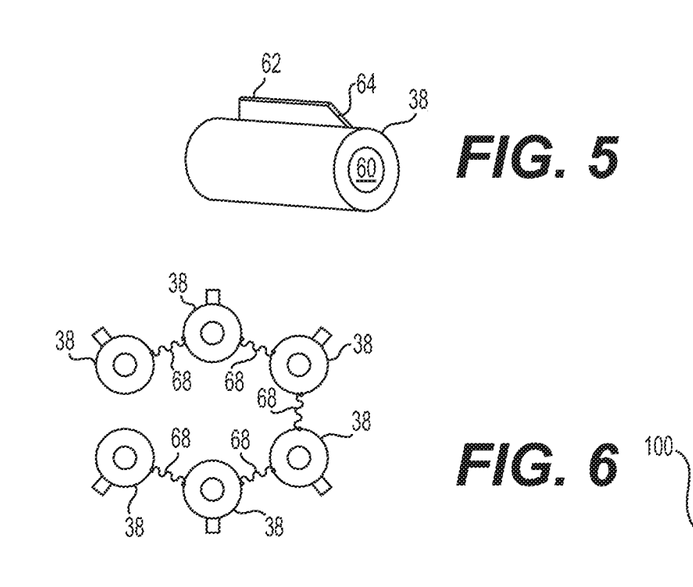
FIG. 5 depicts an exemplary anchor device for use with the medical device of FIG. 1.
FIG. 6 illustrates an exemplary configuration of anchor devices coupled with a suture member.

As shown in FIG. 5, anchor 38 may include a key 62 extending radially outwardly from a central axis of anchor 38. It is understood that while key 62 is illustrated as an elongate bar-shaped member in FIG. 4, other key 62 shapes and structures are within the scope of this disclosure. Additionally, at least a portion 64 of key 62 may be angled, sloped, tapered, arcuate and/or otherwise shaped. As shown in FIG. 4, each key slot 56 of each revolver chamber 36 is configured to correspond in shape to key 62 of each anchor 36. Accordingly, each key slot 56 may cooperate with key 62 of each anchor 38 so as to guide each anchor 38 during deployment via carrier 22.

In some examples, one or more anchors 38 may define a lumen 60 extending therethrough. Lumen 60 may be configured to receive a portion of carrier 22 therein. For example, lumen 60 may be sized such that during actuation, tip 24 of carrier 22 may extend into and through lumen 60 of anchor 38 such that distal-most point 26 may extend through anchor 38 and pierce tissue. As noted above, tip 24 may be tapered. Accordingly, proximal of tip 24, carrier 22 may have a larger dimension (e.g., diameter). As such, once the portion of carrier 22 just proximal of tip 24 is advanced toward anchor 38, the larger dimensioned portion of carrier 22 may engage anchor 38 so as to push anchor 38 distally during deployment.

Figure 7:
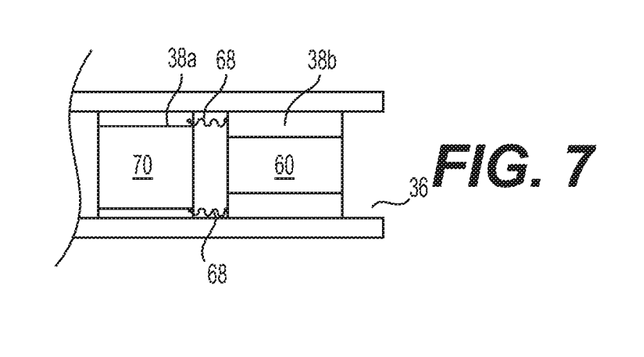
FIG. 7 illustrates an alternative exemplary configuration of anchor devices coupled with a suture member.

Each anchor 38 positioned within each revolver chamber 36 may be coupled together via one or more suture members 68 (not shown in FIG. 4, see FIGS. 6 and 7). For example, as shown in FIG. 6, a proximal end of a first anchor 38 positioned within a first revolver chamber 36 (see FIG. 4) may be coupled via a suture member 68 to a proximal end of an anchor 38 positioned within a second revolver chamber 36 and so forth. As shown in FIG. 6, at least two anchors 38 may be coupled to one single other anchor 38, while the remaining anchors 38 are coupled to two other anchors 38 each to form a strand of anchors 38. In such a manner, each anchor 38 within revolver 34 may be coupled so that a user may sequentially deploy anchors 38 to form a running stitch. In such an arrangement, a user may individually determine the proper location for each anchor 38 to be positioned, and the tension on the suture member 68 between adjacent anchors 38. In other words, a user may actuate actuator 28 a first time to deploy a first anchor 38, and then, if desired, reposition carrier 22 to a second location such that actuation of the actuator 28 a second time may deploy a second anchor 38. Due to the connection of the first and second anchors 38 via suture member(s) 68, a running stitch may be formed in which the distance between positions for anchor 38 deployment determine the degree of pinching (e.g., compression) placed on the tissue to be joined or conversely, the tension experienced by suture member(s) 68.

Additionally and/or alternatively, each revolver chamber 36 may be configured to receive a two-part anchor as shown in FIG. 7. For example, first anchor member 38a and second anchor member 38b may be positioned within a common revolver chamber 36. FIG. 7 depicts a single revolver chamber 36 for clarity. First anchor member 38a may include lumen 70 extending therethrough. Lumen 70 of first anchor member 38a may be dimensioned such that carrier 22 may pass therethrough unobstructed. In other words, lumen 70 may have a dimension (e.g., diameter) sufficiently larger than carrier 22 such that carrier 22 may pass smoothly therethrough. Second anchor member 38b, however, may include lumen 60, similar to lumen 60 described above in reference to FIGS. 4 and 5, extending therethrough. As such, during actuation, tip 24 of carrier 22 may extend into and through lumen 60 of second anchor member 38b so that distal-most point 26 may pierce tissue while a portion of carrier 22 proximal of tip 24 may engage second anchor member 38b so as to push second anchor member 38b distally during deployment. As shown, first anchor member 38a and second anchor member 38b may be coupled together via one or more suture members 68. Accordingly, upon activation of carrier 22 via actuator 28, carrier 22 may extend through first anchor member 38a and push second anchor member 38b into and through tissue, as will be described in further detail below. Due to suture member(s) 68, however, distally advancing second anchor member 38b causes first anchor member 38a to be pulled behind. Accordingly, following deployment, second anchor member 38b will be placed on a distal side of tissue to be joined while first anchor member 38a will be left on a proximal side of tissue to be joined. In other words, the first anchor member 38a and second anchor member 38b may squeeze, pinch, or otherwise join tissue upon deployment.

During use, a user may deliver medical device 10 to a location within a patient in which tissue is to be joined. Medical device 10 may be delivered to such a location through any appropriate manner. For example, medical device 10 may be delivered through a working channel of an insertion device (not shown). Such an insertion device may include any device configured to allow a user to perform medical diagnoses and/or treatments on a patient. For example, the insertion device may include any device configured to allow a user to access and view internal areas of a subject's body. In some examples, the insertion device may be a sterile, single-use, and disposable ureteroscope. Alternatively, the insertion device may be a multiple-use, non-disposable ureteroscope. Other types of devices, however, may be substituted for the ureteroscope, including, as examples, an endoscope, a hysteroscope, a uteroscope, a bronchoscope, a cystoscope, and similar devices. Such devices may be single-use and disposable, or multiple-use and non-disposable. Additionally or alternatively, the insertion device may itself be a medical device and/or include any device configured to deliver medical devices 10. The insertion device may be inserted into one or more of a variety of body openings, lumens, and/or cavities. For example, the insertion device may be inserted into any portion of a urinary tract, such as a ureter, a gastrointestinal lumen, such as an esophagus, a vascular lumen, and/or an airway. Alternatively, medical device 10 may be delivered to a location within a patient in which tissue is to be joined without the use of an insertion device.

Once delivered, a user may position medical device 10 so as to ensure, once actuated, carrier 22 will pass through the desired tissue to be joined. To facilitate proper alignment of carrier 22, an alignment notch or mark (not shown) indicating the position of carrier 22 may be disposed on handle 14. In order to join tissue, the user may actuate actuator 28 so as to distally advance carrier 22. Upon advancement, distal tip 24 of carrier 22 may pierce tissue while carrier 22 pushes an anchor 38 through said pierced tissue and onto the other (e.g., distal) side of the pierced tissue. Upon release of actuator 28, and/or application of force on actuator 28 is ceased by the user, carrier 22 is caused to return towards the retracted state via spring 32, as described above. The linear motion of carrier 22 as it moves proximally may be converted to rotational motion via energy transmission element 46, which in turn causes revolver rod 40 to rotate a predetermined amount, thus rotating revolver 34. Alternatively, revolver 34 may be rotated manually by the user, as described above. Revolver 34 may be rotated such that a first revolver chamber 36 is moved from a position aligned with working channel 20 to a position out of alignment with working channel 20, while moving a second revolver chamber 36 into alignment with working channel 20, as described above.

In an arrangement in which a single anchor 38 is positioned within each revolver chamber 36 (FIG. 6), a user may reposition medical device so as to deploy a second anchor 38 to a second location. Due to suture member 68 coupling adjacent anchors 38, the user may form a running stich to join tissue. Alternatively, in an arrangement in which each revolver chamber 36 houses a two-part anchor 38 (FIG. 7), a single actuation of carrier 22 may be sufficient to join tissue portions together. In either case, medical device 10 may enable tissue joining via its multi-firing anchor 38 arrangement.

Figure 8:
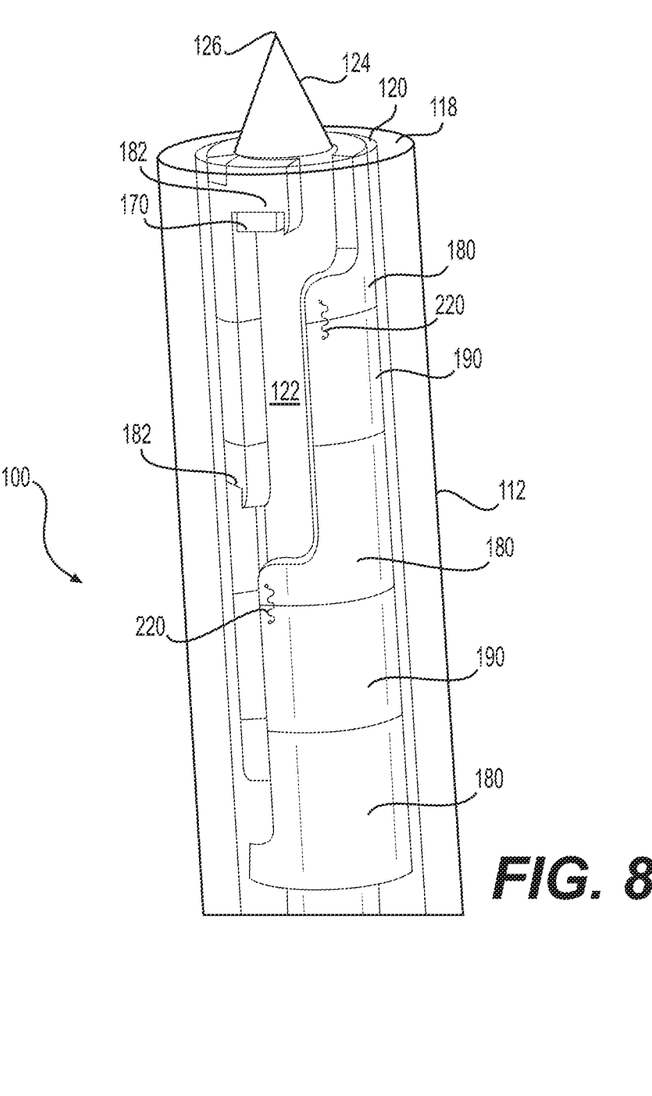
FIG. 8 illustrates a perspective view of a distal end of a medical device according to a second exemplary aspect of the disclosure.

FIGS. 8-13 illustrate an additional example of the present disclosure. As shown in FIG. 8, a medical device 100 may include a luminal body 112. Luminal body 112 may be similar to luminal body 12, described above. For example, luminal body 112 may be coupled to a handle 114 (not shown in FIG. 8) similar to handle 14. Additionally, luminal body 112 may be configured to traverse anatomical lumens of the subject's body. As such, luminal body 112 may include a circular, ovular, irregular, and/or any other cross-sectional shape appropriate for insertion within anatomical lumens of the subject's body, and/or combinations thereof.

Luminal body 112 may include a proximal end 116 (FIG. 9) a distal end 118, and define a working channel 120 extending therebetween. Working channel 120 may be configured to movably receive a carrier 122 therein. Similar to carrier 22, carrier 122 may comprise a longitudinally-extending member such as, for example, a rod. As shown in FIG. 8, one or more anchors 180, 190 may be stacked end-to-end about carrier 122, as will be described in further detail below. Carrier 122 may include a tip 124 which is sharp or pointed such that tip 124 may be configured to pierce bodily tissue as the carrier 122 is advanced, as will be described in further detail below. As shown in FIG. 8, tip 124 may taper distally toward a central distal-most point 126. However, it is understood that tip 124 may have alternative constructions.

Figure 9:
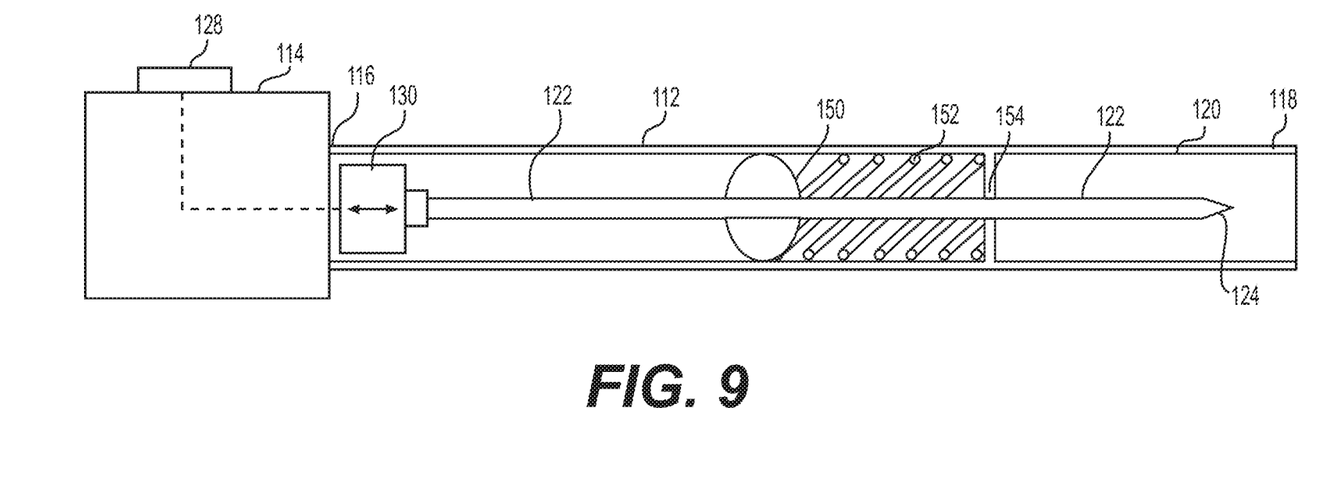
FIG. 9 illustrates the medical device of FIG. 8 in a first state.

Carrier 122 may be comprised of shape memory material and, similar to carrier 22, may be configured to transition between an extended state (FIG. 10) and a retracted state (FIG. 9). Carrier 122 may be caused to move between the extended and retracted states upon manipulation of an actuator 128 (FIG. 9) similar to actuator 28 of FIG. 1. For example, manipulation of actuator 128 in a first direction (e.g., distally), may move carrier 122 distally along and through working channel 120 so as to extend distally beyond distal end 118 of luminal body 112. Once carrier 122 extends distally of luminal body 112, carrier 122 is free to return to its memory configuration. For example, carrier 122 may have a memory configuration similar to the memory configuration of carrier 22 (FIG. 2). Accordingly, carrier 122 may have a rounded, arcuate, bent, or otherwise curved memory configuration. As such, upon exiting working channel 120 and extending distally beyond distal end 118 of luminal body 112, carrier 122 is no longer restrained toward a linear configuration, but may return to its memory curved configuration. In so doing, carrier 122, including tip 124, may pierce through tissue so as to place an anchor 180 and/or 190, as will be described in further detail below.

Additionally, manipulation of actuator 128 in a second direction (e.g., proximally), may cause carrier 122 to move proximally and return towards its retracted state (e.g., a linear configuration) within working channel 120, as shown in FIG. 9. Alternatively, in some examples, manipulation of actuator 128 in a first direction (e.g., distally) may cause carrier 122 to move proximally, while manipulation of actuator 128 in a second direction (e.g., proximally) may cause carrier 122 to move distally. It is understood that actuator 128 may include, by way of non-limiting example, at least one of a slider, a push button, a two-way rocker, a plunger, or any combination thereof.

Carrier 122 may be biased towards its retracted state as shown in FIG. 9. As such, carrier 122 may include a stop member 150 extending radially outwardly of a central longitudinal axis of carrier 122 in the retracted state. Stop member 150 may comprise a protrusion, extension, or any other such component configured to cooperate with a spring 152, at least a portion of which may be positioned about carrier 122. For example, spring 152 may be positioned within working channel 120 of luminal body 112. Additionally, a distal end of spring 152 may be fixed with respect to working channel 120 in any appropriate manner. For example, an inner diameter of working channel 120 may have a reduced portion 154 configured to retain and/or abut the distal end of spring 152. Alternatively, a portion of the distal end of spring 152 may be embedded, secured, or otherwise fixed to an inner diameter surface of working channel 120. When in the retracted state, stop member 150 may rest and/or abut against a proximal end of spring 152 such that spring 152 urges stop member 150, and therefore carrier 122, towards its retracted state within working channel 120. When a user determines a need to move carrier 122 towards its extended state (e.g., when a user determines a need to either pierce tissue and/or place an anchor 180 and/or 190), he/she must apply a force on actuator 128 sufficient to overcome the force of spring 152. Upon application of such a force, stop member 150 may be urged distally against spring 152, thereby compressing spring 152. As spring 152 compresses, a portion of carrier 122 may extend along working channel 120 and distally of luminal body 112 distal end 118 towards its extended state, as shown in FIG. 10.

Figure 10:
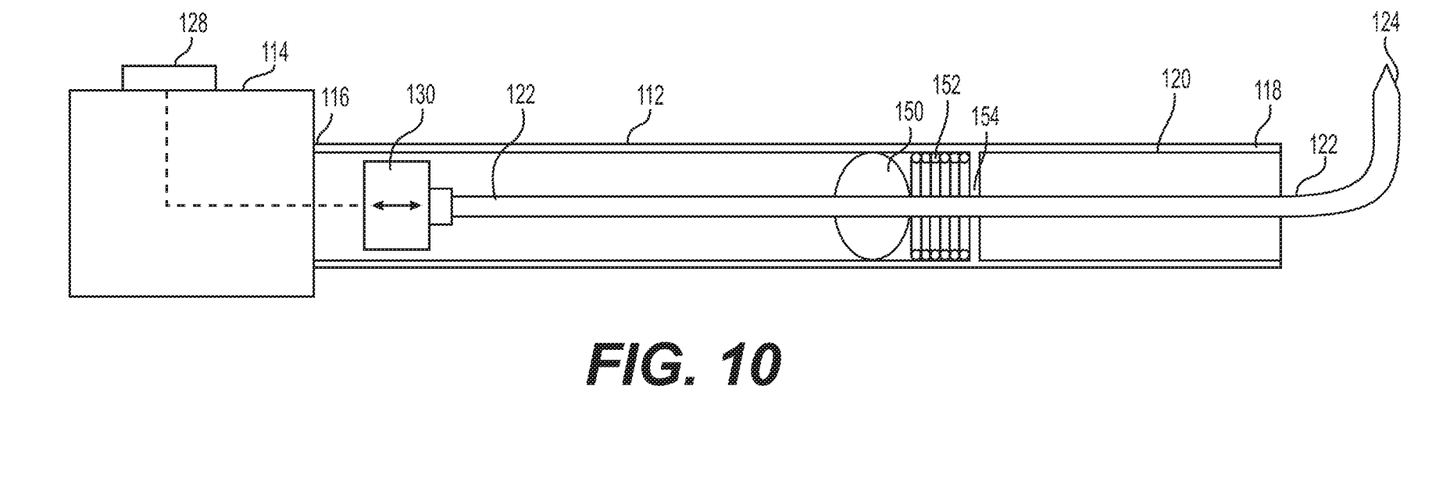
FIG. 10 illustrates the medical device of FIG. 8 in a second state.

In an exemplary aspect, as shown in FIGS. 9 and 10, actuator 128 may be operably coupled to carrier 122 via a mechanism similar to a retractable pen, e.g., a cam follower mechanism 130. For example, actuator 128 may be operably coupled to cam follower mechanism 130 which is in turn operably coupled to carrier 122. One or more portions of cam follower mechanism 130 may be configured to move along luminal body 112 so as to transition carrier 122 between the retracted and extended states. That is, when a user determines a need to move the carrier 122 from the retracted state to the extended state (e.g., when a user determines a need to either pierce tissue and/or place an anchor 180 and/or 190) he/she may manipulate actuator 128 distally to advance one or more portions of cam follower mechanism 130 so as to distally advance carrier 122. Subsequently, additional distal manipulation of actuator 128 may cause one or more portions of cam follower mechanism 130 and carrier 122 to return once again to the retracted state. It is understood that actuation of the carrier 122 in this manner may be repeated any number of times as a user deems necessary. It is understood that while FIGS. 9 and 10 omit various distal details of medical device 100, these details are depicted in FIG. 8.

As shown in FIG. 8, carrier 122 may include a pusher 170 on an exterior circumferential surface of carrier 122. Pusher 170 may be configured to engage with a push anchor 180 to deploy push anchor 180 and optionally, travel anchor 190. For example, pusher 170 may be sized and/or shaped to be received in recess 182 of a first (e.g., distal-most) push anchor 180. In other words, pusher 170 and recess 182 may be configured to cooperate with one another such that pusher 170 fits within recess 182. Accordingly, upon distal advancement of carrier 122, pusher 170 may be received within recess 182 of the first push anchor 180. Due to such engagement, advancement of carrier 122 causes the first push anchor 180 to be deployed as will be described in further detail below.

Figure 11:
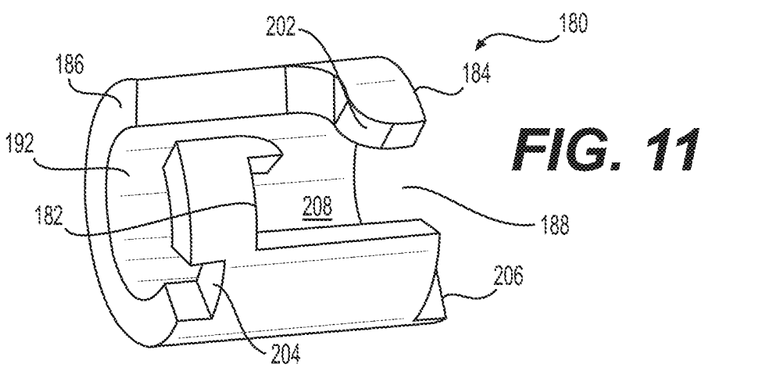
FIGS. 11 and 12 illustrate exemplary anchor devices for use with the medical device of FIG. 8.
Figure 12:
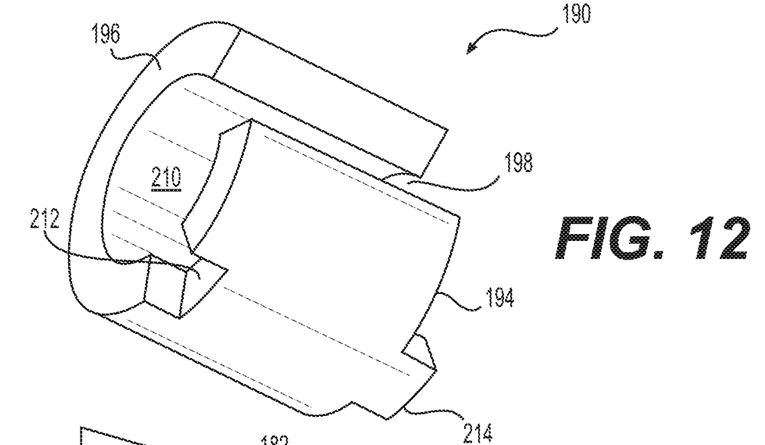

Push anchor 180 and travel anchor 190 are illustrated in FIGS. 11 and 12, respectively. As shown in FIG. 11, push anchor 180 may comprise a proximal end 184, a distal end 186, and define a central lumen 208 extending therebetween. Central lumen 208 may be sized so as to receive carrier 122 therein. Additionally, push anchor 180 may define a passage 188 extending from the proximal end 184 to the distal end 186. As shown, passage 188 may extend between an innermost diameter surface of push anchor 180 to an outermost diameter surface of push anchor 180 so as to extend through the entire wall thickness of push anchor 180. As shown, passage 188 may be at least partially defined by a curved wall 202. During use, as will be described in further detail below, curved wall 202 may guide, direct, or otherwise cooperate with pusher 170 to align pusher 170 with a distal-most push anchor 180.

Push anchor 180 may further define a distal notch 204 and a proximal extension 206. Distal notch 204 may comprise a cut out, recess, or depression in the distal end 186, while proximal extension 206 may be a proximally extending protrusion and/or member. As shown in FIGS. 8 and 11, distal notch 204 and proximal extension 206 may be positioned at different radial locations about a central axis of push anchor 180. In other words, distal notch 204 and proximal extension 206 are misaligned or radially offset from one another.

Travel anchor 190 may comprise a proximal end 194 a distal end 196 and define a central lumen 210 extending therebetween. Central lumen 208 may be sized so as to receive carrier 122 therein. Additionally, travel anchor 190 may define a passage 198 extending from the proximal end 194 to the distal end 196. As shown, passage 198 may extend between an innermost diameter surface of travel anchor 190 to an outermost diameter surface of travel anchor 190 so as to extend through the entire wall thickness of travel anchor 190. As shown, passage 198 may define a linear path from proximal end 194 to distal end 196. Passage 198 may be sized such that pusher 170 may be received therein and move there along from proximal end 194 to distal end 196.

Travel anchor 190 may further define a distal notch 212 and a proximal extension 214. Distal notch 212 may comprise a cut out, recess, or depression in the distal end 196, while proximal extension 214 may be a proximally extending protrusion and/or member. As shown in FIG. 12, distal notch 212 and proximal extension 214 may be aligned along a common radial location about a central axis of travel anchor 190. In other words, distal notch 212 and proximal extension 214 are positioned along a common axis with one another.

As shown in FIG. 8, anchors 180 and 190 may be alternatingly stacked along carrier 122. For example, the proximal extension 206 of a first (e.g., distal-most) push anchor 180 may be received within a distal notch 212 of a first travel anchor 190 while the proximal extension 214 of the first travel anchor 190 is received within the distal notch 204 of a second (e.g., second most distal) push anchor 180. Additionally, this pattern may be repeated until all anchors 180, 190 are positioned about carrier 122. Additionally, one or more anchors 180, 190 positioned about carrier 122 may be coupled to one another via one or more suture members 220. For example, proximal end 184 of a first push anchor 180 may be coupled via a suture member 220 to a distal end 196 of a first travel anchor 190, and so forth. Accordingly, upon activation of carrier 122 via actuator 128, and as described in further detail below, carrier 122 may extend through first travel anchor 190 and push (via pusher 170 within recess 182) first push anchor 180 into and through tissue. Due to suture member(s) 220, however, distally advancing first push anchor 180 causes first travel anchor 190 to be pulled behind. Accordingly, following deployment, first push anchor 180 will be placed on a distal side of tissue to be joined while first travel anchor 190 will be left on a proximal side of tissue to be joined. In other words, first push anchor 180 and first travel anchor 190 may squeeze, pinch, or otherwise join tissue upon deployment.

Figure 13:
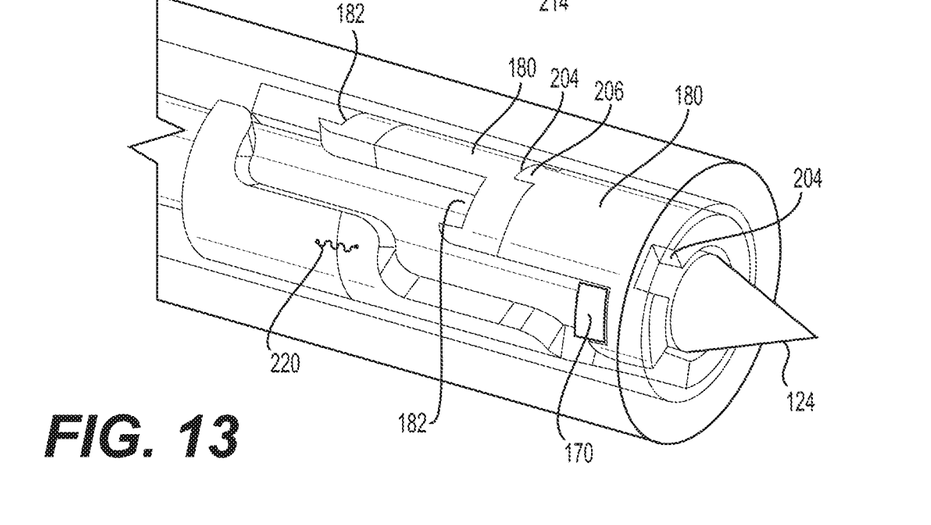
FIG. 13 illustrates an alternative configuration of the distal end of a medical device according to the second exemplary aspect of the disclosure.

Alternatively, as shown in FIG. 13, travel anchors 190 may be omitted. Instead, only push anchors 180 may be stacked on top of one another such that the proximal extension 206 of each push anchor 180 is received within the distal recess 204 of an adjacent push anchor 180. In such an arrangement, one or more, or all of the push anchors 180 may be coupled together via one or more suture members. For example, proximal end 184 of a first push anchor 180 may be coupled via a suture member 220 to the distal end end 186 of an adjacent push anchor 180, and so forth. In such a manner, each push anchor 180 may be coupled so that a user may sequentially deploy anchors 180 to form a running stitch. In such an arrangement, a user may individually determine the proper location for each anchor 180 to be positioned, and the tension on the suture member 220 between adjacent anchors 180.

During use, a user may deliver medical device 100 to a location within a patient in which tissue is to be joined. Medical device 100 may be delivered to such a location through any appropriate manner. For example, similar to medical device 10, medical device 100 may be delivered through a working channel of an insertion device (not shown). Alternatively, medical device 100 may be delivered to a location within a patient in which tissue is to be joined without the use of an insertion device.

Once delivered, a user may position medical device 100 so as to ensure, once actuated, carrier 122 will pass through the desired tissue to be joined. In order to join tissue, the user may actuate actuator 128 so as to distally advance carrier 122. Upon advancement, distal tip 124 of carrier 122 may pierce tissue while pusher 170 distally advances a first (e.g., distal-most) push anchor 180 through said pierced tissue and onto the other (e.g., distal) side of the pierced tissue. In arrangements in which a travel anchor 190 is present (FIG. 8), distally advancing first push anchor 180 causes first (e.g., distal-most) travel anchor 190 to be pulled behind and left on the opposite (e.g., proximal) side of the tissue to be joined.

Upon the return of carrier 122 from the extended state (FIG. 10) to the retracted state (FIG. 9) as described above, pusher 170 may travel proximally along passage 188 of a second (e.g., the next most distal) push anchor 180. As pusher 170 moves along passage 188, curved wall 202 may interact with pusher 170 such that the second push anchor 180 is caused to rotate. That is, the impact of pusher 170 against curved wall 202 may be sufficient to force the second push anchor 180 to rotate. Due to the interaction of proximal extensions 206 and 204 with either distal recess 204 or 212, as described above, rotation of the second push anchor causes likewise rotation of any remaining anchors 180, 190 within medical device 100.

In an arrangement in which only push anchors 180 are used (FIG. 13), a user may reposition medical device 100 so as to deploy subsequent push anchors 180 to an additional location(s), as desired. Due to suture member 220 coupling adjacent push anchors 180, the user may form a running stitch to join tissue. Alternatively, in an arrangement in which travel anchors 190 are used (FIG. 8), a single actuation of carrier 122 may be sufficient to join tissue portions together. In either case, medical device 100 may enable tissue joining due to its multi-firing anchor 180, 190 arrangement.

Figure 14:
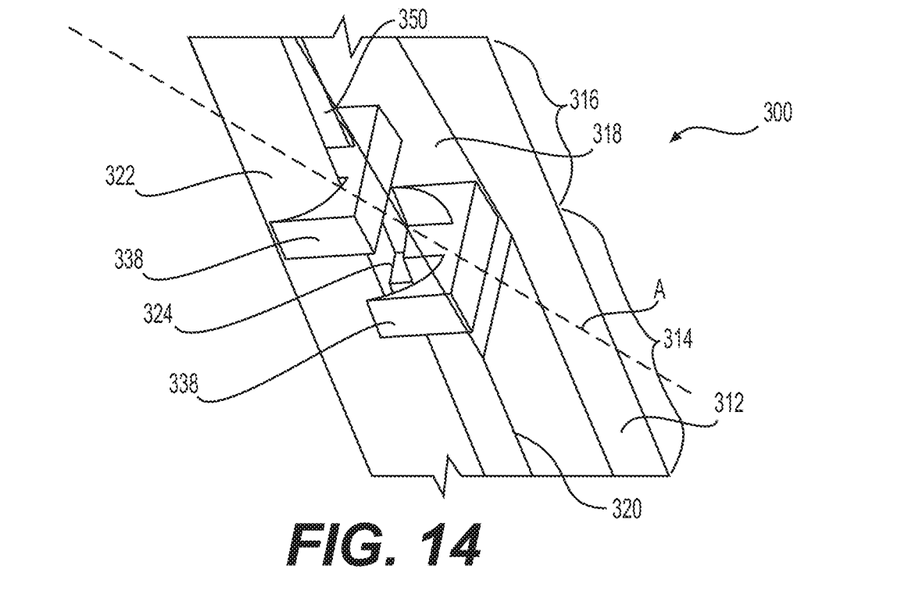
FIG. 14 illustrates a perspective view of a distal end of a medical device according to a third exemplary aspect of the disclosure.
Figure 15:
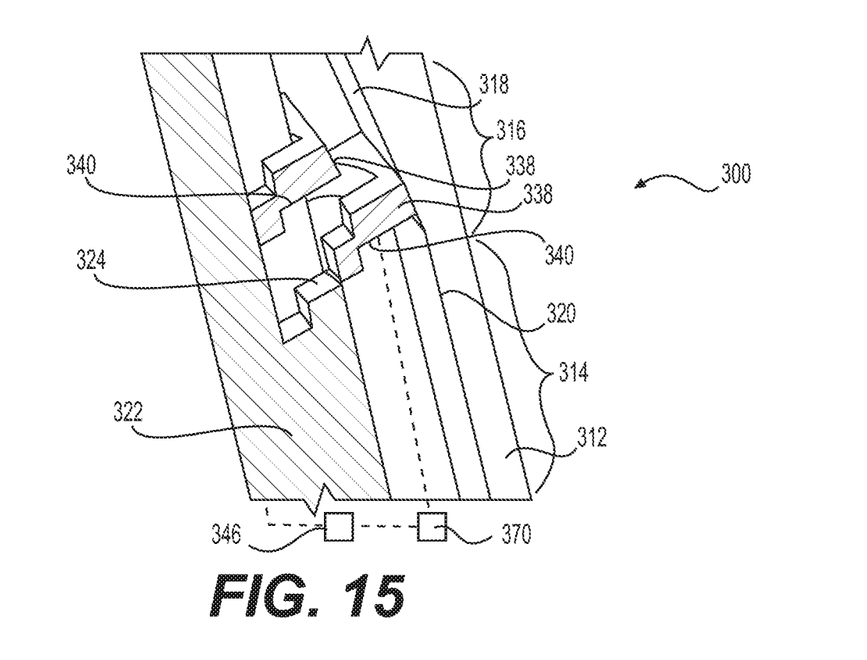
FIG. 15 illustrates a cross-sectional view of the medical device of FIG. 14.

FIGS. 14 and 15 illustrate an additional example of the present disclosure. As shown in FIG. 14, a medical device 300 may include a luminal body 312. Luminal body 312 may be similar to luminal bodies 12 and 112 described above. For example, luminal body 312 may be coupled to a handle (not shown) similar to handles 14, 114. Additionally, luminal body 312 may be configured to traverse anatomical lumens of the subject's body. As such, luminal body 312 may include a circular, ovular, irregular, and/or any other cross-sectional shape appropriate for insertion within anatomical lumens of the subject's body, and/or combinations thereof.

Luminal body 312 may include a proximal end (not shown) a distal end (not shown), and define a working channel 320 extending therebetween. As shown in FIGS. 14 and 15, an internal wall of working channel 320 may be narrowed at constriction 318. For example, an internal dimension (e.g., diameter) of working channel 320 may be reduced via constriction 318. For example, a proximal portion 314 of working channel 320 may have a larger dimension (e.g., diameter) than a distal portion 316 of working channel 320. Constriction 318 may be angled or tapered so as to reduce the dimensions of working channel 320. Additionally, constriction 318 may be configured so as to urge an anchor 338 into engagement with a carrier 322, as will be described in further detail below.

Working channel 320 may be configured to movably receive carrier 322 therein. Similar to carriers 22 and 122, carrier 322 may comprise a longitudinally-extending member such as, for example, a rod. As shown in FIG. 14, however, carrier 322 may further include a geometric feature such as, for example, a recess, groove, or channel 350. Channel 350 may be configured to cooperate with a portion of one or more anchors 338 stacked alongside carrier 322, as will be described in further detail below. That is, once restriction 328 urges anchor 338 toward carrier 322, a portion of anchor 338 may be received within channel 350 and as such, channel 350 may be configured to facilitate anchor 338 engagement with carrier 322. While only two such anchors 338 are illustrated, it is understood that a larger number of anchors 338 may be stacked end to end alongside carrier 322. In addition, one or more of anchors 338 may be coupled together via a suture member (not shown), similar to suture member 68 or 220.

Further, a ratchet 370 may be operably coupled with the luminal body 312 and/or anchors 338 so as to incrementally urge anchors 338 distally along carrier 322. For example, each time carrier 322 returns from the extended state to the retracted state, the ratchet may be activated (e.g., rotated) via an energy transmission element 346, similar to energy transmission element 46 of FIG. 1, so as to distally advance the remaining anchors 338 such that the next most distal anchor 338 may be urged by restriction 318 toward carrier 322 and into channel 350, as described in further detail below. Energy transmission element 346 may be any appropriate element configured to convert a linear force into a rotational force. Examples of such energy transmission elements 346 may include, but are not limited to, a rack and pinion system, a crank, a screw drive, a gearing system, a linkage system, a cam follower mechanism, and any appropriate combinations thereof. Energy transmission element 346 may be configured to convert the linear motion created when carrier 322 returns from the extended state towards the retracted state into rotational movement to activate ratchet 370 to incrementally advance anchors 338 distally along carrier 322.

Once an anchor 338 reaches constriction 318, constriction 318 may urge the anchor 338 radially inwardly towards carrier 322 (e.g., such that a portion of anchor 338 is received within channel 350) for deployment via carrier 322, as will be described in further detail below. Carrier 322 may include a tip (not shown) similar to tips 24 and 124, which is sharp or pointed such that the tip may be configured to pierce bodily tissue as the carrier 322 is advanced distally of working channel 320.

Carrier 322 may be comprised of shape memory material and, similar to carriers 22 and 122, may be configured to transition between an extended state and a retracted state. Carrier 322 may be caused to move between the extended and retracted states in a manner similar to carrier 122 (e.g., via a cam follower mechanism). For example, upon manipulation of an actuator (not shown) in a first direction (e.g., distally), carrier 322 may be distally advanced along and through working channel 320 so as to extend distally beyond the distal end of luminal body 312. Once carrier 322 extends distally of luminal body 312, carrier 322 is free to return to its memory configuration. For example, carrier 322 may have a memory configuration similar to the memory configuration of carrier 22 (FIG. 2). Accordingly, carrier 322 may have a rounded, arcuate, bent, or otherwise curved memory configuration. As such, upon exiting working channel 320 and extending distally beyond the distal end of luminal body 312, carrier 322 is no longer restrained toward a linear configuration, but may return to its memory curved configuration. In so doing, carrier 322, may pierce through tissue so as to place an anchor 138, as will be described in further detail below.

Additionally, manipulation of the actuator in a second direction (e.g., proximally), may cause carrier 322 to move proximally and return towards its retracted state (e.g., a linear configuration) within working channel 320. Alternatively, in some examples, manipulation of the actuator in a first direction (e.g., distally) may cause carrier 322 to move proximally, while manipulation of the actuator in a second direction (e.g., proximally) may cause carrier 322 to move distally.

Carrier 322 and anchor 338 may be configured to cooperate with one another such that carrier 322 may distally advance anchor 338 as carrier 322 transitions from the retracted state to the extended state. Accordingly, carrier 322, as shown in cross-section in FIG. 15, may include a pusher 324 configured to engage a recess 340 of each anchor 338. For example, pusher 324 may be sized and/or shaped to be received in recess 340 of a first (e.g., distal-most) anchor 338. In other words, pusher 324 and recess 340 may be configured to cooperate with one another such that pusher 324 fits within recess 340. For example, each of pusher 324 and recess 340 may have a stepped surface as shown in FIG. 15. Accordingly, upon distal advancement of carrier 322, pusher 324 may be received within recess 340 of the first anchor 338. Due to such engagement, advancement of carrier 322 causes the first anchor 338 to be deployed as will be described in further detail below.

During use, a user may deliver medical device 300 to a location within a patient in which tissue is to be joined. Medical device 300 may be delivered to such a location through any appropriate manner. For example, similarly to medical devices 10 and 100, medical device 300 may be delivered through a working channel of an insertion device (not shown). Alternatively, medical device 300 may be delivered to a location within a patient in which tissue is to be joined without the use of an insertion device.

Once delivered, a user may position medical device 300 so as to ensure, once actuated, carrier 322 will pass through the desired tissue to be joined. In order to join tissue, the user may actuate the actuator so as to distally advance carrier 322. Upon advancement, the distal tip of carrier 322 may pierce tissue while pusher 324 distally advances a first (e.g., distal-most) anchor 338 through said pierced tissue and onto the other (e.g., distal) side of the pierced tissue. In some arrangements, anchors 338 may have varying configurations and are stacked in pairs (coupled therebetween via a suture member) so as to alternate along carrier 322. For example, every other anchor 338 may be a travel anchor (not shown) and include a lumen (not shown) extending therethrough, similar to lumen 70 of first anchor member 38a of FIG. 7. That is, such a travel anchor may be configured similarly to anchor 338, but may not include a portion configured to be received and/or extend within channel 350. As such, carrier 322 may extend through the lumen of the travel anchor unobstructed. Accordingly, in such an arrangement, distally advancing first anchor 338 causes the first (e.g., distal-most) travel anchor to be pulled behind and left on the opposite (e.g., proximal) side of the tissue to be joined.

In an arrangement in which travel anchors are omitted, a user may reposition medical device 300 so as to deploy subsequent anchors 338 to additional locations, as desired. Due to the suture member coupling adjacent anchors 338, the user may form a running stich to join tissue. Alternatively, in an arrangement in which travel anchors are used, a single actuation of carrier 322 may be sufficient to join tissue portions together. In either case, medical device 300 enables tissue joining due to its multi-firing anchor 338 arrangement.

Figure 16:
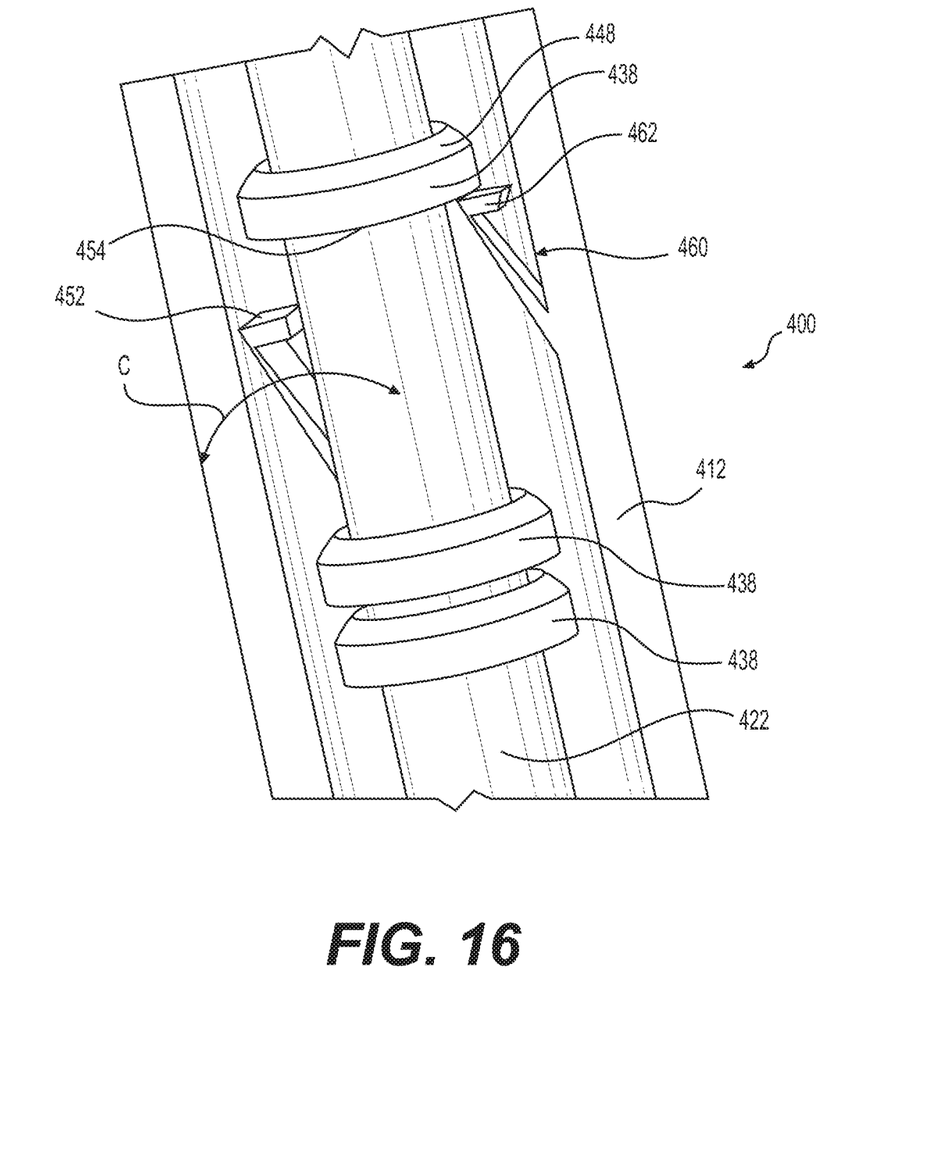
FIG. 16 illustrates a perspective view of a distal end of a medical device according to a fourth exemplary aspect of the disclosure.

FIG. 16 illustrates an additional example of the present disclosure. As shown in FIG. 16, a medical device 400 may include a carrier 422. Similar to carriers 22, 122, and 322, carrier 422 may be received within a luminal body 412. Luminal body 412 may be similar to luminal bodies 12, 112, and 312 described above. For example, luminal body 412 may be coupled to a handle (not shown) similar to handles 14, 114. Additionally, luminal body 412 may be configured to traverse anatomical lumens of the subject's body. As such, the luminal body may include a circular, ovular, irregular, and/or any other cross-sectional shape appropriate for insertion within anatomical lumens of the subject's body, and/or combinations thereof. Further, luminal body 412 may include a living hinge 460 extending radially inwardly toward a central longitudinal axis of luminal body 412 from a position along an inner wall of luminal body 412. Living hinge 460 may move relative to the remainder of luminal body 412. That is, living hinge 460 may rotate towards or away from a central axis of luminal body 412. Living hinge 460 may be biased radially outward of the inner wall of luminal body 412. As will be described in further detail below, living hinge 460 may include support 462 configured to cooperate with a surface 454 of anchor 438.

Luminal body 412 may include a proximal end (not shown) a distal end (not shown), and define a working channel (not shown) extending therebetween configured to movable receive carrier 422 therein. Similar to carriers 22, 122, and 322, carrier 422 may comprise a longitudinally-extending member such as, for example, a rod. As shown in FIG. 16, one or more anchors 438, including tapered, angled, or otherwise machined portions 448, may be stacked about carrier 422. While only three such anchors 438 are illustrated, it is understood that a larger number of anchors 438 may be stacked end to end about carrier 422. In addition, one or more of anchors 438 may be coupled together via a suture member (not shown), similar to suture member 68 or 220. A ratchet (not shown) may be operably coupled with the luminal body so as to incrementally urge anchors 438 distally along carrier 422. For example, each time carrier 422 returns from the extended state to the retracted state, the ratchet may be activated (e.g., via an energy transmission element similar to energy transmission element 46 of FIG. 1) so as to distally advance the remaining anchors 438 such that the next most distal anchor 438 may engage with a living hinge 450, as will be described in further detail below.

Carrier 422 may comprise a member configured to engage and advance anchors 438 distally so as to deploy anchors 438. Carrier 422 may include a tip (not shown) similar to tips 24 and 124, which is sharp or pointed such that the tip may be configured to pierce bodily tissue as the carrier 422 is advanced distally of the working channel. Carrier 322 may be comprised of shape memory material and, similar to carriers 22 and 122, may be configured to transition between an extended state and a retracted state. Carrier 422 may be caused to move between the extended and retracted states in a manner similar to carrier 122 (e.g., via a cam follower mechanism). For example, upon manipulation of an actuator (not shown) in a first direction (e.g., distally), carrier 422 may be distally advanced along and through the working channel so as to extend distally beyond the distal end of luminal body 412. Once carrier 422 extends distally of luminal body 412, carrier 422 is free to return to its memory configuration. For example, carrier 422 may have a memory configuration similar to the memory configuration of carrier 22 (FIG. 2). Accordingly, carrier 422 may have a rounded, arcuate, bent, or otherwise curved memory configuration. As such, upon exiting the working channel and extending distally beyond the distal end of luminal body 412, carrier 422 is no longer restrained toward a linear configuration, but may return to its memory curved configuration. In so doing, carrier 422, may pierce through tissue so as to place an anchor 438, as will be described in further detail below.

Additionally, manipulation of the actuator in a second direction (e.g., proximally), may cause carrier 422 to move proximally and return towards its retracted state (e.g., a linear configuration) within the working channel. Alternatively, in some examples, manipulation of the actuator in a first direction (e.g., distally) may cause carrier 422 to move proximally, while manipulation of the actuator in a second direction (e.g., proximally) may cause carrier 422 to move distally.

Carrier 422 may include living hinge 450 as shown in FIG. 16. Living hinge 450 may move relative to the remainder of carrier 422 in the direction of arrow C as shown in FIG. 16. That is, living hinge 450 may rotate towards or away from a central axis of carrier 422. Living hinge 450 may be biased radially outward of carrier 422. Carrier 422 and anchor 438 may be configured to cooperate with one another such that carrier 422 may distally advance anchor 438 as carrier 422 transitions from the retracted state to the extended state. Accordingly, living hinge 450 may include a pusher 452 configured to cooperate with a surface 454 of anchor 438. That is, pusher 452 may be shaped so as to engage (e.g., abut) surface 454 of anchor 438. Accordingly, upon distal advancement of carrier 422, pusher 452 may engage surface 454 of the first anchor 438 (e.g., distal-most anchor 438) and bias living hinge 460 radially away from the central longitudinal axis of luminal body 412. Due to such engagement, advancement of carrier 422 causes the first anchor 438 to be deployed as will be described in further detail below. As the carrier 422 returns from the extended state towards the retracted state, living hinge 450 will be biased towards carrier 422 as a second anchor 438 (e.g., the next most distal anchor) moves (e.g., slides) over living hinge 450. The second anchor 438 will move relative to the carrier 422 until surface 454 extends just distally of support 462, at which point, an anchor hinge guide (not shown) of the second anchor 438 may guide living hinge 460 to expand toward a central longitudinal axis of luminal body 412 and guide living hinge 450 to expand radially outward of carrier 422. For example, the hinge guide may include an angled recess on the inner diameter of the anchor 438 at the distal end thereof, and configured to cooperate with the distal end of living hinge 460. As such, living hinge 460 will retract proximally beyond a first anchor 438 and spring open slightly upon being received in the hinge guide at the distal end of second anchor 438. This slight opening of living hinge 460 will allow pusher 462 to contact surface 454 of the first anchor 438 so that, upon actuation of carrier 422, first anchor 438 can be urged distally by living hinge 450, and moved distally.

During use, a user may deliver medical device 400 to a location within a patient in which tissue is to be joined. Medical device 400 may be delivered to such a location through any appropriate manner. For example, similarly to medical devices 10 100, and 300, medical device 400 may be delivered through a working channel of an insertion device (not shown). Alternatively, medical device 400 may be delivered to a location within a patient in which tissue is to be joined without the use of an insertion device.

Once delivered, a user may position medical device 400 so as to ensure, once actuated, carrier 422 will pass through the desired tissue to be joined. In order to join tissue, the user may actuate the actuator so as to distally advance carrier 422. Upon advancement, the distal tip of carrier 422 may pierce tissue while pusher 452 of living hinge 450 distally advances a first (e.g., distal-most) anchor 438 through said pierced tissue and onto the other (e.g., distal) side of the pierced tissue. In some arrangements, anchors 438 may have varying configurations and are stacked in pairs (coupled therebetween via a suture member) so as to alternate along carrier 422. For example, every other anchor 438 may be a travel anchor (not shown) and include a lumen (not shown) extending therethrough, similar to lumen 70 of first anchor member 38a of FIG. 7. As such, living hinge 450 may extend through the lumen of the travel anchor unobstructed. Accordingly, in such an arrangement, distally advancing first anchor 438 causes the first (e.g., distal-most) travel anchor to be pulled behind and left on the opposite (e.g., proximal) side of the tissue to be joined.

In an arrangement in which travel anchors are omitted, a user may reposition medical device 300 so as to deploy subsequent anchors 438 to additional locations, as desired. Due to the suture member coupling adjacent anchors 438, the user may form a running stich to join tissue. Alternatively, in an arrangement in which travel anchors are used, a single actuation of carrier 422 may be sufficient to join tissue portions together. In either case, medical device 400 enables tissue joining due to its multi-firing anchor 438 arrangement.

While exemplary aspects of anchors 38, 180, 190, 338, and 438 have been described throughout, it is understood that numerous modifications of 38, 180, 190, 338, and 438 may be employed without departing from the scope of this disclosure. For example, the cross-sectional shape of any such anchor may be modified. Additionally, in some examples, a distal surface of one or more of anchors 38, 180, 190, 338, and 438 may include a sharp edge configured to pierce tissue. In such an arrangement, tips 24 and 124 may not be sharp.

While principles of the present disclosure are described herein with reference to illustrative examples for particular applications, it should be understood that the disclosure is not limited thereto. Those having ordinary skill in the art and access to the teachings provided herein will recognize additional modifications, applications, arrangement, and substitution of equivalents all fall within the scope of the examples described herein. Accordingly, the disclosure is not to be considered as limited by the foregoing description.

What is claimed is:

1. A medical device, comprising:
  a luminal body defining a working channel extending between a proximal end of the luminal body and a distal end of the luminal body;
  a rotatable member disposed within the working channel;
  a carrier defining a pusher thereon, wherein the carrier is configured to transition between a first state and a second state, when in the first state, a distal portion of the carrier is disposed within the working channel along a central longitudinal axis of the working channel, and when in the second state, the distal portion of the carrier extends distally of the luminal body and the rotatable member at an angle with respect to the longitudinal axis; and a plurality of anchors, each anchor of the plurality of anchors disposed about the carrier, wherein at least a distal-most anchor of the plurality of anchors defines a surface configured to cooperate with the pusher, and wherein at least the distal-most anchor of the plurality of anchors further defines a curved wall configured to cooperate with the pusher to rotate the plurality of anchors.

2. The medical device of claim 1, wherein the carrier is comprised of a shape memory material.

3. The medical device of claim 1, wherein the carrier has a distal tip configured to pierce tissue.

4. The medical device of claim 3, wherein the distal tip of the carrier is configured to be passed through a central lumen of each of the plurality of anchors.

5. The medical device of claim 1, wherein the plurality of anchors comprises at least the distal most anchor and a travel anchor, wherein the travel anchor is coupled to the distal most anchor via at least one suture member.

6. The medical device of claim 1, wherein each anchor of the plurality of anchors defines a recess configured to cooperate with the pusher, and wherein each anchor of the plurality of anchors defines a curved wall configured to cooperate with the pusher to rotate the plurality of anchors.

7. The medical device of claim 6, wherein each anchor of the plurality of anchors is coupled to an adjacent anchor of the plurality of anchors via at least one suture member.

8. The medical device of claim 1, further comprising: a handle coupled to the proximal end of the luminal body and including an actuator operably coupled with the carrier to move the carrier between the first and second states.

9. The medical device of claim 8, wherein the actuator is operably coupled to the carrier via a cam follower mechanism.

10. The medical device of claim 1, wherein each anchor of the plurality of anchors define a proximal extension and a distal recess.

11. The medical device of claim 10, wherein the proximal extension of each anchor of the plurality of anchors is configured to be matingly received within the distal recess of an adjacent anchor of the plurality of anchors.

12. The medical device of claim 10, wherein the proximal extension and distal recess of at least some of the plurality of anchors are radially offset from one another while the proximal extension and distal recess of the remaining anchors of the plurality of anchors are aligned along a common axis.

13. A medical device, comprising:

a luminal body defining a working channel extending between a proximal end of the luminal body and a distal end of the luminal body;

a revolving member defining a plurality of chambers therein, the revolving member being rotatably coupled to the distal end of the luminal body;

a carrier configured to transition between a first state and a second state, wherein:

when in the first state, a distal portion of the carrier is disposed within the working channel along a central longitudinal axis of the working channel, and when in the second state, the distal portion of the carrier is configured to extend distally of the luminal body and the revolving member in a curved configuration; and a plurality of anchors, at least one anchor of the plurality of anchors being positioned within each chamber of the plurality of chambers; and a handle assembly including an actuator operably coupled with the carrier and an energy transmission element operably coupled with the revolving member, wherein linear movement of the carrier may result in rotational movement of the revolving member via the energy transmission element.

14. The medical device of claim 13, wherein the carrier is comprised of a shape memory material.

15. The medical device of claim 13, wherein the revolving member defines six chambers.

* * * * *